US008147871B2

(12) United States Patent
Brown et al.

(10) Patent No.: US 8,147,871 B2
(45) Date of Patent: Apr. 3, 2012

(54) PHARMACEUTICAL FORMULATIONS

(75) Inventors: Adrian Brown, Harlow (GB); Wayne M. Matthews, Harlow (GB); Daniel M. Margetson, Harlow (GB); Stephen Mark McAllister, Harlow (GB); Ronald K. Raby, Collegeville, PA (US)

(73) Assignee: Capsugel Belgium BVBA (BE)

( * ) Notice: Subject to any disclaimer, the term of this patent is extended or adjusted under 35 U.S.C. 154(b) by 1471 days.

(21) Appl. No.: 11/078,077

(22) Filed: Mar. 11, 2005

(65) Prior Publication Data
US 2005/0249807 A1   Nov. 10, 2005

Related U.S. Application Data

(60) Provisional application No. 60/552,499, filed on Mar. 12, 2004.

(51) Int. Cl.
*A61K 9/20* (2006.01)
*A61K 9/28* (2006.01)
*A61K 9/48* (2006.01)
*A61K 9/52* (2006.01)
*A61K 9/58* (2006.01)
*A61K 9/32* (2006.01)

(52) U.S. Cl. ........ 424/464; 424/441; 424/451; 424/457; 424/462; 424/463; 424/465; 424/482

(58) Field of Classification Search .................. 424/464
See application file for complete search history.

(56) References Cited

U.S. PATENT DOCUMENTS

| | | | |
|---|---|---|---|
| 3,186,910 A | 6/1965 | Glassman |
| 3,228,789 A | 1/1966 | Glassman |
| 3,314,809 A | 4/1967 | Klug et al. |
| 3,394,983 A | 7/1968 | Greif et al. |
| 3,399,803 A | 9/1968 | Oglevee et al. |
| 3,723,312 A | 3/1973 | Hay, Jr. |
| 3,779,942 A | 12/1973 | Bolles |
| 4,196,565 A | 4/1980 | Bodenmann et al. |
| 4,250,097 A | 2/1981 | Pfister |
| 4,281,763 A | 8/1981 | Pace |
| 4,351,825 A | 9/1982 | Sothmann et al. |
| 4,417,591 A | 11/1983 | Culver |
| 4,487,327 A | 12/1984 | Grayson |
| 4,498,080 A | 2/1985 | Culver |
| 4,543,138 A | 9/1985 | Bollinger et al. |
| 4,550,238 A | 10/1985 | Van Herle et al. |
| 4,557,180 A | 12/1985 | Glomeau |
| 4,564,363 A | 1/1986 | Bagnall et al. |
| 4,576,284 A | 3/1986 | Wittwer |
| 4,591,475 A | 5/1986 | Tomka et al. |
| D285,837 S | 9/1986 | Wittwer |
| 4,625,513 A | 12/1986 | Glomeau |
| 4,655,840 A | 4/1987 | Wittwer et al. |
| 4,673,438 A | 6/1987 | Wittwer et al. |
| 4,678,516 A | 7/1987 | Alderman et al. |
| 4,696,163 A | 9/1987 | Glomeau |
| 4,705,695 A | 11/1987 | Lehmann et al. |
| 4,724,019 A | 2/1988 | Brown et al. |
| 4,737,357 A | 4/1988 | Lehmann et al. |
| 4,738,724 A | 4/1988 | Wittwer et al. |
| 4,738,817 A | 4/1988 | Wittwer et al. |
| 4,764,378 A | 8/1988 | Keith et al. |
| 4,766,728 A | 8/1988 | Glomeau |
| 4,790,881 A | 12/1988 | Wittwer et al. |
| 4,792,451 A | 12/1988 | Kim |
| 4,793,493 A | 12/1988 | Makiej et al. |
| 4,795,644 A | 1/1989 | Zentner |
| 4,801,460 A | 1/1989 | Goertz et al. |
| 4,806,337 A | 2/1989 | Snipes et al. |
| 4,833,221 A | 5/1989 | Albrecht et al. |
| 4,899,516 A | 2/1990 | Krieger et al. |
| 4,928,840 A | 5/1990 | Barshay et al. |
| 4,936,461 A | 6/1990 | Makiej et al. |
| 4,964,262 A | 10/1990 | Moser et al. |
| 5,004,601 A | 4/1991 | Snipes |
| 5,074,426 A | 12/1991 | Goodhart et al. |
| 5,082,655 A | 1/1992 | Snipes et al. |
| 5,085,033 A | 2/1992 | Graham |
| 5,110,877 A | 5/1992 | Hoess et al. |
| 5,135,752 A | 8/1992 | Snipes |
| 5,139,790 A | 8/1992 | Snipes |
| 5,155,172 A | 10/1992 | Siol et al. |
| 5,219,931 A | 6/1993 | Siol et al. |
| 5,225,202 A | 7/1993 | Hodges et al. |

(Continued)

FOREIGN PATENT DOCUMENTS

BE    900950    4/1985

(Continued)

OTHER PUBLICATIONS

U.S. Appl. No. 10/598,810, filed Sep. 12, 2006, Brown et al. Cuff et al., Pharmaceutical Technology, Jun. 1998 pp. 96-106.
Hu, et al., Journal of Drug Targeting, vol. 7 (3) pp. 223-232 (1999).
Fukui et al., Int. J. Pharm vol. 217, 2001, pp. 33-43.
Kohri et al., Int. J. Pharm 49(3): 213-221 (1989).
Meyuys et al., Euro J. Pharm. Sci., vol. 24, 2005, pp. 207-212.
Nakamichi et al., J. Drug Delivery Sci & Tech. vol. 14, No. 3, pp. 193-198.
U.S. Appl. No. 10/470,438, filed Jan. 6, 2004, McAllister et al.
U.S. Appl. No. 10/470,439, filed Jan. 20, 2004, MacAllister et al.
U.S. Appl. No. 10/060,603, filed Jan. 30, 2002, McAllister et al.
U.S. Appl. No. 12/689,015, Clark, et al.
U.S. Appl. No. 12/741,596, Brown, et al.

*Primary Examiner* — Robert A Wax
*Assistant Examiner* — Randeep Singh
(74) *Attorney, Agent, or Firm* — Finnegan, Henderson, Farabow, Garrett & Dunner, LLP

(57) ABSTRACT

The present invention is directed to novel pharmaceutically acceptable polymeric compositions suitable for melt extrusion and injection molding of single or multi-component pharmaceutical dosage forms comprising a plurality of drug substance containing sub-units, being capsule compartments and/or solid sub-units comprising a solid matrix of a polymer which contains a drug substance, the sub-units being connected together in the assembled dosage form.

32 Claims, No Drawings

U.S. PATENT DOCUMENTS

| | | | |
|---|---|---|---|
| 5,236,689 A | 8/1993 | Wong et al. | |
| RE34,390 E | 9/1993 | Culver | |
| 5,244,668 A | 9/1993 | Snipes | |
| 5,270,397 A | 12/1993 | Rhein et al. | |
| 5,280,073 A | 1/1994 | Siol et al. | |
| 5,312,008 A | 5/1994 | Davis | |
| 5,312,388 A | 5/1994 | Wong et al. | |
| 5,387,421 A | 2/1995 | Amidon et al. | |
| 5,443,461 A | 8/1995 | Atkinson et al. | |
| 5,456,919 A | 10/1995 | Patell et al. | |
| 5,489,436 A | 2/1996 | Hoy et al. | |
| 5,548,033 A | 8/1996 | Vetter et al. | |
| 5,552,159 A | 9/1996 | Mueller et al. | |
| 5,644,011 A | 7/1997 | Lehmann et al. | |
| 5,652,316 A | 7/1997 | May et al. | |
| 5,672,359 A | 9/1997 | Digenis et al. | |
| 5,674,530 A | 10/1997 | Amidon et al. | |
| 5,705,189 A | 1/1998 | Lehmann et al. | |
| 5,741,519 A | 4/1998 | Rosenberg et al. | |
| 5,750,143 A | 5/1998 | Rashid et al. | |
| 5,769,267 A | 6/1998 | Duynslager et al. | |
| 5,770,224 A | 6/1998 | Rashid et al. | |
| 5,837,780 A | 11/1998 | Albrecht et al. | |
| 5,939,099 A | 8/1999 | Grabowski et al. | |
| 5,976,571 A | 11/1999 | Crison et al. | |
| 6,063,821 A | 5/2000 | Breitenbach et al. | |
| 6,139,875 A | 10/2000 | Adams et al. | |
| 6,153,218 A | 11/2000 | Barnwell et al. | |
| 6,200,600 B1 | 3/2001 | Rashid | |
| 6,207,191 B1 | 3/2001 | Crison et al. | |
| 6,248,807 B1 | 6/2001 | Sosa et al. | |
| 6,270,797 B1 * | 8/2001 | Gidwani et al. | 424/457 |
| 6,284,803 B1 * | 9/2001 | Kothrade et al. | 514/772.1 |
| 6,287,470 B1 | 9/2001 | Vetter et al. | |
| 6,290,990 B1 | 9/2001 | Grabowski et al. | |
| 6,309,666 B1 | 10/2001 | Hatano et al. | |
| 6,318,650 B1 * | 11/2001 | Breitenbach et al. | 241/23 |
| 6,322,816 B1 | 11/2001 | Zeidler et al. | |
| 6,355,712 B1 | 3/2002 | Schultes et al. | |
| 6,367,228 B1 | 4/2002 | Wurst et al. | |
| 6,368,629 B1 | 4/2002 | Watanabe et al. | |
| 6,387,401 B2 | 5/2002 | Rosenberg et al. | |
| 6,517,866 B1 * | 2/2003 | Am Ende et al. | 424/457 |
| 6,528,089 B1 | 3/2003 | Kothrade et al. | |
| 6,548,513 B1 | 4/2003 | Creekmore et al. | |
| 6,551,617 B1 | 4/2003 | Corbo et al. | |
| 6,576,255 B1 | 6/2003 | Petereit et al. | |
| D481,456 S | 10/2003 | McAllister et al. | |
| D493,518 S | 7/2004 | McAllister et al. | |
| 6,765,046 B1 | 7/2004 | Numrich et al. | |
| 6,797,283 B1 * | 9/2004 | Edgren et al. | 424/472 |
| D501,549 S | 2/2005 | McAllister et al. | |
| D501,550 S | 2/2005 | McAllister et al. | |
| 6,890,993 B2 | 5/2005 | Schultes et al. | |
| D506,545 S | 6/2005 | McAllister et al. | |
| D516,714 S | 3/2006 | McAllister et al. | |
| 7,014,810 B2 | 3/2006 | Krull et al. | |
| 7,163,693 B1 | 1/2007 | Clarke et al. | |
| 7,217,381 B2 | 5/2007 | Sowden | |
| 7,691,407 B2 | 4/2010 | Clarke et al. | |
| 2001/0008637 A1 | 7/2001 | Hochrainer et al. | |
| 2002/0160042 A1 | 10/2002 | Petereit et al. | |
| 2003/0029558 A1 | 2/2003 | Hochrainer et al. | |
| 2003/0049311 A1 | 3/2003 | McAllister et al. | |
| 2003/0068369 A1 | 4/2003 | McAllister et al. | |
| 2003/0143257 A1 * | 7/2003 | Fleshner-Barak et al. | 424/426 |
| 2003/0194428 A1 | 10/2003 | Miller et al. | |
| 2003/0194429 A1 | 10/2003 | Miller et al. | |
| 2003/0194430 A1 | 10/2003 | Miller et al. | |
| 2003/0194431 A1 | 10/2003 | Miller et al. | |
| 2004/0013697 A1 * | 1/2004 | Berndl et al. | 424/401 |
| 2004/0104501 A1 | 6/2004 | Petereit et al. | |
| 2004/0115256 A1 | 6/2004 | MacAllister et al. | |
| 2004/0131668 A1 | 7/2004 | Hochrainer et al. | |
| 2004/0166153 A1 | 8/2004 | McAllister et al. | |
| 2005/0008690 A1 | 1/2005 | Miller et al. | |
| 2005/0080188 A1 | 4/2005 | Schultes et al. | |
| 2005/0175687 A1 | 8/2005 | McAllister et al. | |
| 2005/0267250 A1 | 12/2005 | Theil et al. | |
| 2006/0052515 A1 | 3/2006 | Schultes et al. | |
| 2006/0057201 A1 | 3/2006 | Bonney et al. | |
| 2006/0121248 A1 | 6/2006 | Lorenz et al. | |
| 2006/0147714 A1 | 7/2006 | Schultes et al. | |
| 2006/0177496 A1 | 8/2006 | McAllister et al | |
| 2007/0055017 A1 | 3/2007 | Schultes et al. | |
| 2007/0066708 A1 | 3/2007 | Goldacker et al. | |
| 2007/0087049 A1 | 4/2007 | Clarke et al. | |
| 2007/0112135 A1 | 5/2007 | Wicker et al. | |
| 2007/0122624 A1 | 5/2007 | Schultes et al. | |
| 2007/0123610 A1 | 5/2007 | Schultes et al. | |
| 2007/0222117 A1 | 9/2007 | Hoess et al. | |
| 2007/0276093 A1 | 11/2007 | Schultes et al. | |
| 2008/0260814 A1 | 10/2008 | Petereit et al. | |
| 2009/0108492 A1 | 4/2009 | McAllister | |
| 2009/0110721 A1 | 4/2009 | McAllister | |
| 2009/0110723 A1 | 4/2009 | McAllister | |
| 2009/0148514 A1 | 6/2009 | McAllister | |
| 2009/0148518 A1 | 6/2009 | Brown et al. | |
| 2010/0074947 A1 | 3/2010 | Brown et al. | |

FOREIGN PATENT DOCUMENTS

| | | |
|---|---|---|
| CA | 2211671 | 2/1996 |
| CA | 2253695 | 11/1998 |
| CA | 2253700 | 11/1998 |
| CA | 2257547 | 7/1999 |
| DE | 3524963 | 1/1987 |
| DE | 3543912 | 6/1987 |
| DE | 3727894 | 7/1990 |
| EP | 0091908 | 4/1983 |
| EP | 141397 | 10/1984 |
| EP | 0211079 | 1/1985 |
| EP | 143524 | 6/1985 |
| EP | 0228067 | 12/1986 |
| EP | 0 364 060 | 4/1990 |
| EP | 0410422 | 7/1990 |
| EP | 0759303 | 4/1995 |
| EP | 0 727 205 | 8/1996 |
| EP | 0 759 303 | 2/1997 |
| EP | 1266655 A | 12/2002 |
| FR | 1454013 | 8/1965 |
| FR | 2524311 | 4/1982 |
| GB | 1496737 | 6/1975 |
| GB | 2172569 | 3/1985 |
| GB | 2187703 | 9/1987 |
| NL | 7610038 | 9/1976 |
| WO | WO 90/12567 | 11/1990 |
| WO | WO 92/13521 | 8/1992 |
| WO | WO 94/09743 | 5/1994 |
| WO | WO 95/13056 | 5/1995 |
| WO | 95/16438 | 6/1995 |
| WO | 96/15775 | 5/1996 |
| WO | 96/24337 | 8/1996 |
| WO | 97/33569 | 9/1997 |
| WO | WO 99/27909 | 6/1999 |
| WO | 01/08666 | 2/2001 |
| WO | WO 01/39751 | 6/2001 |
| WO | WO 01/43935 | 6/2001 |
| WO | WO 02/098625 | 12/2002 |
| WO | WO 03/043601 | 5/2003 |
| WO | 2005/070401 | 8/2005 |
| WO | 2006/107593 | 10/2006 |

* cited by examiner ical U.S. Ser. No. 60/552,499 filed 12 Mar. 2004.

PHARMACEUTICAL FORMULATIONS

This application claims the benefit of priority from provisional U.S. Ser. No. 60/552,499 filed 12 Mar. 2004.

FIELD OF THE INVENTION

This invention relates to the preparation of injection molded single or multi-component dosage forms using novel pharmaceutically acceptable polymeric blends.

BACKGROUND OF THE INVENTION

Various types of pharmaceutical dosage forms are known for oral dosing. Pharmaceutical capsules are well known, generally being intended for oral dosing. Such capsules generally comprise an envelope wall of a pharmaceutically acceptable, e.g. orally ingestible, polymer material such as gelatin, although other materials for capsule walls, e.g. starch and cellulose based polymers are also known. Such capsules generally have soft walls made by making a film on a capsule former, which is then allowed to dry. Rigid walled capsules made by injection molding are also known, see for example U.S. Pat. Nos 4,576,284; 4,591,475; 4,655,840; 4,738,724; 4,738,817 and 4,790,881 (all to Warner Lambert). These disclose specific constructions of capsules made of gelatin, starch and other polymers, and methods of making them by injection molding of hydrophilic polymer—water mixtures. U.S. Pat. No. 4,576,284 specifically discloses such capsules provided with a cap which closes the capsule, and which is formed in situ on the filled capsule by molding. U.S. Pat. No. 4,738,724 discloses a wide range of rigid capsule shapes and parts.

Multi-compartment capsules, including those of the type where each compartment has different drug release characteristics, or for example, contains a different drug substance or formulation are also known, for example in U.S. Pat. No. 4,738,724 (Warner-Lambert); U.S. Pat. No. 5,672,359 (University of Kentucky); U.S. Pat. No. 5,443,461 (Alza Corp.); WO 95/16438 (Cortecs Ltd.); WO 90/12567 (Helminthology Inst.); DE-A-3727894, and BE 900950 (Warner Lambert); FR 2524311, and NL 7610038 (Tapanhony NV); FR 1,454, 013 (Pluripharm); U.S. Pat. No. 3,228,789 (Glassman); and U.S. Pat. No. 3,186,910 (Glassman) among others. U.S. Pat. No. 4,738,817 discloses a multicompartment capsule with a similar construction to those of U.S. Pat. No. 3,228,789 and U.S. Pat. No. 3,186,910, made of a water-plasticized gelatin. U.S. Pat. No. 4,738,817 ('817) Witter et al., U.S. Pat. No. 4,790, 881 ('881), Wittwer et al., and EP 0 092 908, Wittwer, F., all discloses injection molded capsules prepared with gelatin and other excipients. Wittwer et al. '817 and '881 also prepare capsules with other hydrophilic polymers, such as hydroxypropylmethyl-cellulose phthalate (HPMCP), methylcellulose, microcrystalline cellulose, polyethylene glycol, cellulose acetate phthalate (CAP) and with polyvinylpyrrolidone. Both U.S. Pat. No. 4,790,881 and EP 0 091 908 propose other polymers having enteric properties suitable for use, including generally acrylates and methacrylates (Eudragits) although none are demonstrated and no specific details are provided.

Pharmaceutical dosage forms are also known which comprise a matrix of a solid polymer, in which a drug substance is dispersed, embedded or dissolved as a solid solution. Such matrixes may be formed by an injection molding process. This technology is discussed in Cuff G, and Raouf F, Pharmaceutical Technology, June (1998) pages 96-106. Some specific formulations for such dosage forms are disclosed in U.S. Pat. Nos. 4,678,516; 4,806,337; 4,764,378; 5,004,601; 5,135,752; 5,244,668; 5,139,790; 5,082,655; 5,552,159; 5,939,099; 5,741,519; 4,801,460; 6,063,821; WO 99/27909; CA 2,227,272; CA 2,188,185; CA 2,211,671; CA 2,311,308; CA 2,298,659; CA 2,264,287; CA 2,253,695; CA 2,253,700; and CA 2,257,547 among others.

U.S. Pat. No. 5,705,189, is directed to a group of copolymers of methacrylic acid, methyl methacrylate and methyl acrylate, for use as thermoplastic agents in the production of drugs coatings, and capsules. No information is presented on the quality of the capsule formation with respect to warping or other distortions produced by the injection molding process. Nor is shear rate data presented for the viscosity/temperature figures of the emulsions presented therein.

It would also be desirable to prepare a pharmaceutical dosage form in which a pharmaceutically acceptable polymeric blend is extruded by hot melt into a suitable dosage form, or is injection molded into suitable dosage forms, which may be multicompartmental, such as in a capsule. This pharmaceutical polymeric composition as the dosage form may provide differing physio-chemical characteristics for each segment containing an active agent, such that a convenient dosage form can be optioned which may include a rapid dissolve, immediate, delayed, pulsatile, or modified release which can be produced by simply selecting the appropriate polymer(s) to be molded for each section.

SUMMARY OF THE INVENTION

The present invention provides for novel pharmaceutical compositions, and their use in melt extrusion technologies, and in the making of injection molded capsule shells, linkers, spacers, multicomponent injection molded capsule shells, linkers or spacers, multicomponent pharmaceutical dosage forms, and other aspects as defined in the claims and description of this application.

Another embodiment of the invention is to provide an alternative and improved pharmaceutical dosage form which provides, inter alia, greater flexibility in the dosage form adapted to a patient's specific administration requirement, using the novel formulations, or compositions, of pharmaceutically acceptable polymers and suitable excipients in said dosage forms.

Another embodiment of the invention is to provide a process of producing the multicomponent dosage forms comprising the novel pharmaceutically acceptable polymeric blends by injection molding. These multi-component dosage forms are suitable for containing a pharmaceutically acceptable active agent, or agents, for release thereby.

In accordance with the invention, a melt extrusion composition, and an injection molded capsule shell, and/or linker is provided for, with a composition, preferably including Eudragit RL 100 or Eudragit RS 100 or a combination thereof.

The capsule or linker, comprises a solid matrix, and preferably comprises Eudragit RL 100 present in an amount of about 10 to 80% w/w, and a hydroxypropyl cellulose derivative, or blend of hydroxypropyl celluloses, from about 30 to about 70% w/w.

The composition may optionally further comprises dissolution-modifying excipients present in an amount of about 0% w/w to about 30% w/w; a lubricant present in an amount up to about 30% w/w; a plasticizer present in an amount up to about 10% w/w, and a processing agent present in an amount up to about 10% w/w.

In an alternative embodiment, the pharmaceutical dosage form comprises a plurality of sub-units, each being a drug substance-containing capsule compartment. In this case, each compartment is physically separated from at least one adjacent compartment, preferably by a wall made of a pharmaceutically acceptable polymer material. In the case in which at least one of the sub-units is a drug substance-containing capsule compartment its wall thickness is in the range of about 0.1-0.8 mm. In another embodiment the wall thickness is in the range of about 0.3-0.8 mm.

The multi-component dosage form of the invention affords a high degree of versatility in that it can be composed of various combinations of different dosage forms having different release characteristics. For example, the sub-units can be a substantially immediate release sub-unit, a sustained release sub-unit, or a pulsed release sub-unit.

Other objects and advantages of the invention will be apparent from the following description.

DETAILED DESCRIPTION OF THE INVENTION

The present invention is directed to novel compositions of a pharmaceutically acceptable polymer and excipients, which polymeric composition may be injection molded into one or more components which can optionally be utilized together, such as in a stacked or multi-component dosage form. It is recognized that the polymeric blends may be injection molded into a single component that may also contain the active agent for oral administration.

The present invention also relates to the application of a pharmaceutically acceptable film coating over a component comprising the novel pharmaceutically acceptable polymeric blends as described herein. The film coating may be a delayed release formulation, or a pH control formulation as are well known in the art. One suitable coating is Opradry, and/or Eudragit L30D-55. The enteric coatings, represented by application of L30D-55 for instance, may be applied using standard equipment such as a GMP Aerocoater column coater. The component weight gain is nominally from about 3% to about 5% w/w.

The pharmaceutically acceptable polymeric blends herein are designed to provide consistent dissolution profiles.

A suitable multicomponent dosage form is disclosed in PCT/EP00/07295, filed Jul. 27, 2000, published as WO 01/08666 on Feb. 8, 2001, the contents of which are incorporated by reference herein in its entirety.

The parts of the dosage form of this invention, e.g. a capsule compartment wall, a solid sub-unit, or a closure or linker, comprise a pharmaceutically acceptable polymeric blend (and adhesive material if adhesive welds are formed) which is generally regarded as safe, e.g. for oral ingestion and is capable of being formed into the required shape of a capsule compartment wall, a solid sub-unit, or a closure or linker as described above. A preferred method of forming the polymer material into the desired shape is injection molding, which may be a hot or cold runner injection molding process. Suitable injection molding machines for such a process are known.

The pharmaceutical dosage form may comprises a plurality of capsule compartments each bounded and physically separated from at least one adjacent compartment by a wall made of a pharmaceutically acceptable polymer material, such as described herein, adjacent compartments being connected together in the assembled dosage form, and being retained together by the connection at least prior to administration to a patient, one or more of the compartments containing a drug substance. Suitably in the assembled dosage form of this first embodiment there are at least two, for example three, such capsule compartments. Three or more such compartments may be linearly disposed in the assembled dosage form, e.g. in an arrangement comprising two end compartments at opposite ends of the line, and one or more intermediate compartments. Suitably there may be two such capsule compartments. Suitably one of such two capsule compartments may be made of a material which is a sustained release component, i.e. so that the capsule compartment wall dissolves, bursts or is otherwise breached to release its contents after a time delay, e.g. when the compartment has reached the intestine. Suitably the other of such two capsule compartments may be made of a material which is an immediate release component, i.e. so that the capsule compartment wall dissolves, bursts or is otherwise breached to release its contents immediately or effectively immediately, e.g. when the compartment is in the mouth or stomach.

One or more, e.g. all, of the capsule compartments may for example be substantially cylindrical, which term includes shapes which have a circular, oval or oblate circular cross section across the longitudinal axis, and shapes which have parallel or tapering e.g. with side walls which taper conically over at least part of their extent. Such substantially cylindrical capsule compartments may be provided with connectable parts at one or both of their longitudinally disposed ends so that the assembled dosage form may also be overall of a substantially cylindrical shape.

Suitably, methacrylic acid copolymers (such as Eudragit E®, Eudragit E100® Eudragit® L and/or Eudragit® S), poly (meth)acrylate copolymers (such as Eudragit® 4135F, and 4155F), and ammonium methacrylate copolymers (such as Eudragit® RL and/or Eudragit® RS), are used for hot melt extrusion and injection molding. The group of poly(meth) acrylate copolymers, such as Eudragit® RS 100 or RL100 are an embodiment of this invention.

Acrylic and/or methacrylic acid-based polymers which are soluble in intestinal fluids and which can be formed into capsules are for example disclosed in U.S. Pat. No. 5,705,189 (Roehm GmbH) the content of which is incorporated herein by reference in its entirety. These poly(meth)acrylate copolymers were extrudable and injection molded into capsule half's wherein the ratio of acrylic and/or methacrylic acid was generally 20% w/w or more of the copolymer (Examples 1-8). In these Examples, glycerol monostearate was added on a 1-6% wt base of the polymer as the sole mold-releasing agent. The Lehmann patent teaches that unblended polymers alone are not suitable for injection molding, but must be blended with a lubricant to produce a capsule shell therein.

In order to produce injection molded, non-distorted, unwarped capsule/sub-unit components for assembly into either single capsule or multicompartment dosage forms using Eudragit RS100 or RL100, it has been determined that at least one lubricant and dissolution modifying agent are useful to obtain release from the injection molds.

The polymer Eudragit RL100 is described by the manufacturer, Rohm Pharma, as being a highly permeable pH independent polymer which granules are insoluble in water. Eudragit RS 100 is also described as being a pH independent polymeric granule with low permeability, and insoluble in water. In contrast, Eudragit 4135F/4155F dissolves only above pH 7, e.g. in the colon, therefore suitable for use as a sustained or delayed release component, and the polymer Eudragit E100 dissolves in acid and is suitable for use as an immediate release component.

These and other pharmaceutically acceptable polymers are described in detail in the Handbook of Pharmaceutical excipients, published jointly by the American Pharmaceutical association and the Pharmaceutical society of Britain.

The RL100 polymer is blended with additional excipients which include, but are not limited to, swelling agents, such as HPMC, HPC, etc.; surfactants, such as SDS or the Pluronic group of agents; pore-forming/chanelling agents, such as lactose or PEG; additional polymers for co-blending such as RS100; and additional buffering agents for adjust of microclimate pH conditions.

In one embodiment of the invention is a co-blend of RL100 with the polymer HPC, such as that marketed by Aqualon, a division of Hercules Incorporated, as Klucel®. Klucel HPC is produced in various grades, determined by their intended use. Suitable Klucel polymers are Klucel EF, Klucel JH, Klucel LF, and Klucel GF. Klucel E has a viscosity in the range of 150-700 (a 300-6-mPas for EF pharm/EXF Pharm), and a molecular weight of about 80,000; J has a viscosity of 150-400 and a molecular weight of about 140,000, L has a viscosity in the range of 75-150, and a molecular weight of about 95,000; and G has a viscosity in the range of 75 400, and a molecular weight of about 370,000.

Addition of these thermoplastic polymers to the blend provides for reduced sensitivity to welding conditions, improved tensile properties both pre and post hydration, and a more robust swelling of the polymer at pH of 1 to 6.

It is recognized that the formulations of co-blends still require additional excipients as herein described. One such excipient is a lubricant, such as stearyl alcohol.

It has been determined that these coblended polymers produces shells which hydrate and swell considerably more than the non-blended polymeric composition under a number of conditions. This produces a formulation which has significant improvements in dissolution reproducibility; the release of the capsule shells is influenced less by the weld settings; an enhanced hydration profile, which results in less structural integrity upon dissolution; and superior appearances, and tensile properties of the resulting shells.

The Eudragit RL100 co-blended components have further been found to be stable after prolonged storage conditions.

It is recognized that the polymeric compositions are first melted in a melt extrusion process, and may also contain additional additives or excipients to assists in melt flow, strength, brittleness, and other molding characteristics, these additional excipients include but are not limited to, plasticizers, absorption enhancers, additional surfactants, flavouring agents, dyes, etc. Therefore, another aspect of the present invention is a pharmaceutical composition for melt extrusion comprising Eudragit RL100 or RS100 and a lubricant, such as stearyl alcohol.

While the compositions herein may be molded in varying wall-thickness, it is preferably that capsules or components have a wall-thickness of about 0.3 to about 0.8 mm, suitably 0.5 mm. However, dissolution performance will more appropriately tailor the wall thickness depending upon the release profiles desired. Increases in wall thickness may be necessary to reduce warping of the components, or modification of the additional excipients in addition to this may be necessary.

The polymer polymethacyrlate, Eudragit RL100 or RS 100 is present in the formulation in an amount of about 10 to about 80% w/w. In another embodiment Eudragit RL100 or RS 100is present in an amount of about 20 to about 50% w/w. In another embodiment Eudragit RL100 or RS 100 is present in an amount of about 20 to 40% w/w.

As noted, the polymeric material(s) may include other substances to modify their properties and to adapt them to various applications, including but not limited to surfactants, absorption enhancers, lubricants, plasticizers, dissolution modifying agents, processing aids, colouring agents, flavouring agents and sweetening agents. Incorporation of a surfactant into the formulation may be necessary or desired to lower the viscosity and surface tension of the formulation/blend, however, in higher amounts it may adversely effect the quality of the resulting dosage form. The surfactant selection may be guided by HLB values but is not necessarily a useful criterion. While HLB surfactants have been utilized herein, such as Tween® 80 (HLB=10), Pluronic F68 (HLB=28), and SDS (HLB>40), lower HLB value surfactants, such as Pluronic F92 and F127 may also be used. Pluronic, made by BASF, USA has a synonym of POLOXAMER. Pluronic F68 for instance has a molecular weight of 8,400. Pluronic F127 has a molecular weight of 12,600. Pluronics are polyoxypropylene-polyoxyethylene block copolymers.

A surfactant may also be called an oligomeric surface modifier and includes, but is not limited to: Pluronics® (block copolymers of ethylene oxide and propylene oxide, and are also referred to as polyoxypropylene-polyoxyethylene block copolymers); lecithin, Aerosol OT® (sodium dioctyl sulfosuccinate), sodium lauryl sulfate, Polyoxyl 40® hydrogenated castor oil, polyoxyethylene sorbitan fatty acid esters, i.e., the polysorbates such as Tween®, such as Tween 20, 60 & 80, the sorbitan fatty acid esters, i.e., sorbitan monolaurate, monooleate, monopalmitate, monostearate, etc. such as Span® or Arlacel®, Emsorb®, Capmul®, or Sorbester®, Triton X-200, polyethylene glycol's, glyceryl monostearate, Vitamin E-TPGS® (d-alpha-tocopheryl polyethylene glycol 1000 succinate), sucrose fatty acid esters, such as sucrose stearate, sucrose oleate, sucrose palmitate, sucrose laurate, and sucrose acetate butyrate, etc.; and combinations and mixtures thereof.

Suitably, the formulation may optionally contain from about 0 to about 10% w/w surfactant(s). Suitable surfactants for use herein include, sodium lauryl sulfate, also referred to as sodium dodecyl sulfate (SDS) or a block copolymers of ethylene oxide and propylene oxide, or mixtures thereof. In one embodiment, suitable surfactants are Vitamin E-TPGS®, sodium lauryl sulfate, sucrose fatty acid esters, lecithin, and the Pluronic groups. In another embodiment, if SDS (Texapon K-12®) or a block copolymers of ethylene oxide and propylene oxide is used in the formulation, they are present in an amount less than 2% by weight, suitably, less than 1% w/w.

The polymeric carriers or oligomeric surface modifiers, if appropriately chosen, may themselves act as absorption enhancers. Suitable absorption enhancers for use herein, include but are not limited to, chitosan, lecithin, lectins, sucrose fatty acid esters such as the ones derived from stearic acid, oleic acid, palmitic acid, lauric acid, and Vitamin E-TPGS, and combinations or mixtures thereof. Suitably, these absorption enhancers are present in a range of about 0 to about 20% w/w.

Plasticizers may be employed to assist in the melting characteristics of the composition. Exemplary of plasticizers that may be employed in this invention are triethyl citrate (TEC), triacetin, tributyl citrate, acetyl triethyl citrate (ATEC), acetyl tributyl citrate (ATBC), dibutyl phthalate, dibutyl sebacate (DBS), diethyl phthalate, vinyl pyrrolidone glycol triacetate, polyethylene glycol, polyoxyethylene sorbitan monolaurate, propylene glycol, or castor oil; and combinations or mixtures thereof. The polymeric material will determine which plasticizer is suitable for use. Suitably, the plasticizer is present in an amount of about 0 to about 20% w/w. In one embodiment of the invention the plasticizers are present in an amount from about 0 about 5% w/w. One embodiment of the present invention is the ability to form an injection molded shell of a Eudragit RL 100 or RS 100 formulation without the addition of a plasticizer such as those noted above.

Dissolution modifying agents, or substances that assist in release modification, alter the erosion and/or swelling characteristics of the capsule shell/linker/component. Many different classes of agents may be used, such as the known disintegrants represented by "Explotab" (sodium starch glycollate), "Kollidon-CL", (cross-linked PVP), Kollidon VA 64 (copovidone) commercially available from BASF, Starch 1500, swelling agents such as polyvinyl pyrrolidone (PVP, also know as POVIDONE, USP), manufactured by ISP-Plasdone or BASF-Kollidon, primarily Grades with lower K values (K-15, K-25, but also K-30 to K-90), cellulosic derivatives such as hydroxypropyl methyl cellulose (HPMC), wicking agents such as low molecular weight solutes, e.g. mannitol, lactose, and starch; inorganic salts such as sodium chloride (typically at 5-10%).

Kollidan VA 64, or copovidone, is also known as copolyvidone, copovidonum, copovidone or copovidon, is ratio of two monomers, vinylpyrrolidone and vinyl acetate.

Another class of agents of dissolution modification agents for use herein are known as swellable solids, and include but are not limited to poly(ethylene)oxide, the cellulosic derivatives, such as ethyl cellulose and cellulose acetate phthalate; hydroxypropylcellulose (HPC), such as the lower molecular weights, e.g., KLUCEL EF and LF grades, and mixtures of the lower molecular weights with higher molecular weight grades such as JF or GF; hydroxypropylmethyl cellulose (HPMC), and other hydroxyalkylcellulose derivatives. Suitably, the swellable solids used as dissolution modifying excipients are in the range of about 10% to about 70% w/w. In another embodiment the swelling agents is present in an amount from about 20 to about 65% w/w, suitably about 50% w/w.

Other suitable dissolution modifying excipients include, but are not limited to the class of non-reducing sugars, such as xylitol, or mannitol, present in the range of about 2.5 to about 15% w/w. Also included herein are a class of water soluble fillers, such as lactose, lactitol, maltitol, sorbitol or alternatively organic acids such as malic acid, citric acid or succinic acid, suitably present in the range of about 5 to about 70% w/w. In another embodiment of the present invention the water soluble fillers may be present from an amount of about 5 to about 20% w/w Another group of suitable dissolution modifying excipients are the agents generally referred to as disintegrants, such as sodium starch glycolate, croscarmellose sodium NF (Aci-Di-Sol® produced by FMC), copovidone, and crospovidone (cross-linked polyvinyl pyrrolidone); and combinations or mixtures thereof. Suitably, the class of disintegrants are present in the range of about 10 to 40%, more preferably about 20 to 30% w/w. It is recognized that the one of more classes of dissolution modifying excipients may be used alone, or in combination as mixtures with each other, resulting in a range from about 2.5 to about 70% w/w.

One such combination is hydroxypropylcellulose and lactose. Additional regents, generally classified as processing aids, include strengthening agents, such as talc. Suitably, the processing aids are present from about 0 to about 10% w/w. In another embodiment, the processing aids are present from about 0 to about 5% w/w.

Suitable mold processing lubricants or glidants for use herein, include but are not limited to, stearyl alcohol, stearic acid, glycerol monostearate (GMS), talc, magnesium stearate, silicon dioxide, amorphous silicic acid, and fumed silica; and combinations or mixtures thereof. The lubricant functions primarily as a flow promoter for the composition. One embodiment of the present invention is the use of stearyl alcohol as a suitable lubricant. Suitably, a commercial grade of stearyl alcohol, such as Crodacol S95 (Croda Oleochemicals) is used herein. The lubricant materials should also be suitable for milling. The amount of lubricant present in the formulation is from about 0 to about 30% w/w. In another embodiment the lubricant is present from about to about 25% w/w. In another embodiment, the lubricant is present from about 10 to 15% w/w.

Stearyl alcohol has been found to act as a mold processing lubricant but and causes no mold distortion, i.e. crumpling of the multidosage compartment shell when the hot soft shell is taken out of the mold. Another alternative material useable as a lubricant/flow promoter is lecithin (a natural product). Suitably, the lubricants for use herein do not introduce any metal ion contamination.

One embodiment of the present invention is the combination of stearyl alcohol, at least one swellable solid, and the polymer Eudragit RL100. Optionally, the formulation may further comprise a surfactant, such as SDS at 2% w/w or less, or 1% or less. The swellable solid may be the polymer hydroxypropylcellulose or a blend of hydroxypropylcellulose.

The final products of this invention, i.e. the capsules, and or components or sub-units may additionally include materials in the polymer materials of which they are made to enhance the ease with which they can be welded together. The sub-units may additionally be provided with constructional features and/or include materials in the polymer materials of which they are made to enhance the ease with which they can be joined together, either by simple mechanical joints, or welded together. A suitable material for assisting such are opacifier materials such as carbon (e.g. 0.2-0.5%), iron oxides or titanium dioxide (e.g. 0.5-1.0%) which help the polymer to absorb laser energy. Such opacifier materials are generally regarded as safe.

For example each of a plurality of sub units, e.g. of the capsule compartments, solid sub-units, or combinations thereof may comprise the same or different polymer(s). For example each of a plurality of sub units, e.g. of capsule compartments, solid sub-units, or combinations thereof may comprise the same or different drug substance. For example each sub-unit may contain the same drug substance but release the contents into the gastro-intestinal tract of the patient at a different rate, at different times after administration to the patient or at different places in the patient's gastro-intestinal system. Alternatively each sub-unit may contain a different drug substance, each of which may be released at the same or a different rate or time after administration or place in the patient's gastro-intestinal system.

For example two or more sub-units, e.g. two capsule compartments, may each contain different drug substances, and/or different drug substance formulations, and/or the same drug in different formulations, so that a combination of two or more drug substances or formulations may be administered to a patient.

The dosage form of this invention enables the assembly together of sub-units which differ in their drug content and/or drug content release characteristics to provide a dosage form tailored to specific administration requirements.

The dimensions and shape of each of the sub-units and hence of the overall assembled dosage form may be determined by the nature and quantity of the material to be contained therein and the intended mode of administration and intended recipients. For example a dosage form intended for oral administration may be of a shape and size similar to that of known capsules intended for oral administration.

The dosage form is particularly suitable for presentation as an oral dosage form containing one or more drug substances suitable for oral administration, and appears to be suitable for all types of such drug substance.

The drug substance(s) contained in any capsule compartment may be present in any suitable form, e.g. as a powder, granules, compact, microcapsules, gel, syrup or liquid provided that the capsule compartment wall material is sufficiently inert to the liquid content of the latter three forms. The contents of the compartments, e.g. drug substances, may be introduced into the compartments by standard methods such as those used conventionally for filling capsules, such as dosating pins or die filling.

The sub-units may differ from each other in their drug content release characteristics, and this may be achieved in various ways. For example one or more solid sub-units and/or capsule compartments may be substantially immediate release, i.e. releasing their drug contents substantially immediately upon ingestion or on reaching the stomach. This may for example be achieved by means of the matrix polymer or the capsule compartment wall dissolving, disintegrating or otherwise being breached to release the drug content substantially immediately. Generally, immediate-release sub-units are preferably provided by being capsule compartments.

For example one or more solid sub-units and/or capsule compartments may be sustained-release sub-units. Preferably these are solid sub-units, as a bulk matrix of polymer is likely to dissolve or disperse more slowly to release its drug content that a thin walled capsule.

For example one or more solid sub-units and/or capsule compartments may be pulsed-release sub-units for example releasing their drug content at a specific predetermined point in a patient's gastro-intestinal system. This may be achieved by the use of polymer materials which dissolve or disperse only at defined pH environments, such as the above mentioned Eudragit® polymers. For instance, E100 is acid labile.

For example in the above-described capsule compartment-linker-capsule compartment dosage form one capsule compartment may be effectively immediate release and the other may be sustained, delayed or pulsed release. To achieve this for example one capsule compartment may be made of polymer materials which cause the capsule compartment to release its drug content in the stomach or upper part of the digestive tract, and the linker (acting as a closure for the second compartment) and the second compartment itself may be made of materials e.g. the above described enteric polymers, which release their drug content only in the intestinal environment.

Determination of the time or location within the gastro-intestinal tract at which a sub-unit releases its drug substance content may be achieved by for example the nature of the sub-unit material, e.g. a solid sub-unit matrix polymer or a capsule compartment wall material, or in the case of an end compartment which is closed by a closure, by the nature of the closure material. For example the wall of different, e.g. adjacent, compartments may be made of polymers which are different or which otherwise differ in their dissolution or disintegration characteristics so as to endow different compartments with different drug release characteristics. Similarly for example the polymer matrix material of different, e.g. adjacent, solid sub-units may be made of polymers which are different or which otherwise differ in their dissolution or disintegration characteristics so as to endow different solid sub-units with different drug release characteristics.

For example the matrix, wall or closure material may be a polymer which dissolves or disperses at stomach pH to release the drug substance in the stomach. Alternatively the wall material of different compartments may differ so that different compartments have different release characteristics.

For example a solid sub-unit or a capsule compartment may have respectively a matrix or a wall or a closure comprising an enteric polymer which dissolves or disperses at the pH of the small or large intestine to release the drug substance in the intestine. Suitable such polymers have been described above, for example, with reference to U.S. Pat. No. 5,705, 189.

Additionally or alternatively the wall material may differ in thickness between compartments so that thicker walled compartments disrupt more slowly than thinner walled compartments.

Additionally or alternatively the compartment walls or the closure may have areas or points of weakness which preferentially dissolve and may thereby determine the time of onset and/or rate of release of the drug substance content. For example such points of weakness may comprise holes, e.g. small holes, e.g. laser-drilled holes in the compartment wall or the closure, these holes being closed and/or covered with a film of a polymer material that dissolves at a pre-determined point in the digestive tract, for example an enteric polymer material. For example such points of weakness may comprise thinned parts in a capsule compartment wall formed during the molding operation in which the capsule compartment is formed.

The sub-units may additionally or alternatively have surface or other constructional features that modify their drug release characteristics. For example solid sub-units may be provided with internal cavities or channels to create a large surface area. For example solid sub-units may be in the form of hollow cylinders, donuts, or toroids, which shapes are known to tend towards first-order dissolution or erosion in liquid media and correspondingly to tend toward first-order release of drug content dispersed therein.

"Pharmaceutically acceptable agents" includes, but is not limited to, drugs, proteins, peptides, nucleic acids, nutritional agents, as described herein. This term includes therapeutic active agents, bioactive agents, active agents, therapeutic agents, therapeutic proteins, diagnostic agents, or drug(s) as defined herein, and follows the guidelines from the European Union Guide to Good Manufacturing Practice. Such substances are intended to furnish pharmacological activity or other direct effect in the diagnosis, cure, mitigation, treatment, or prevention of a disease or to affect the structure and function of the body. The substance may also include a diagnostic agent, such as an imaging agent and/or a radioactive labeled compound. Their use may be in a mammal, or may be in a human. The pharmacological activity may be prophylactic, or for treatment of a disease state. The agents herein include both small molecule therapeutics, as well as peptides and proteins. The pharmaceutical compositions described herein may optionally comprise one or more pharmaceutically acceptable active agent, bioactive agent, active agent, therapeutic agent, therapeutic protein, diagnostic agent, or drug(s) or ingredients distributed within.

As used herein the term's "active agent", "drug moiety" or "drug" are all used interchangeably.

Water solubility of an active agent is defined by the United States Pharmacoepia. Therefore, active agents which meet the criteria of very soluble, freely soluble, soluble and sparingly soluble as defined therein are encompassed this invention.

Suitable drug substances can be selected from a variety of known classes of drugs including, but not limited to, analgesics, anti-inflammatory agents, anthelmintics, anti-arrhythmic agents, antibiotics (including penicillin's), anticoagulants, antidepressants, antidiabetic agents, antiepileptics, antihistamines, antihypertensive agents, antimuscarinic agents, antimycobactefial agents, antineoplastic agents, immunosuppressants, antithyroid agents, antiviral agents, anxiolytic sedatives (hypnotics and neuroleptics), astringents, beta-adrenoceptor blocking agents, blood products and substitutes, cardiac inotropic agents, corticosteroids, cough suppressants (expectorants and mucolytics), diagnostic agents, diuretics, dopaminergics (antiparkinsonian agents), haemostatics, immunological agents, lipid regulating agents, muscle relaxants, parasympathomimetics, parathyroid calcitonin and biphosphonates, prostaglandins, radiopharmaceuticals, sex hormones (including steroids), anti-allergic agents, stimulants and anorexics, sympathomimetics, thyroid agents, PDE IV inhibitors, NK3 inhibitors, CSBP/RK/p38 inhibitors, antipsychotics, vasodilators and xanthines.

Preferred drug substances include those intended for oral administration and intravenous administration. A description of these classes of drugs and a listing of species within each class can be found in Martindale, The Extra Pharmacopoeia, Twenty-ninth Edition, The Pharmaceutical Press, London, 1989, the disclosure of which is hereby incorporated herein by reference in its entirety. The drug substances are commercially available and/or can be prepared by techniques known in the art.

The polymeric blends can be preferably selected from known pharmaceutical polymers. The physico-chemical characteristics of these polymers, as well as the thickness of the ultimate injection molded component, will dictate the design of the dosage form, such as rapid dissolve, immediate release, delayed release, modified release such as sustained release, controlled release, or pulsatile release. etc.

The polymer blends are made by well-known methods for producing hot melt extrusions in which the selected ingredients are fed into a feed hopper of an extrusion machine. Suitable well known equipment is readily available for producing a hot melt extrusion of the blends herein.

For production of an early release capsule or component in a multidosage capsule, (such as in a 2 hour window or less), the polymer Eudragit RL 100 (Röhm), may be extruded into a thin walled component shell (such as those indicated herein), by blending with the excipients as noted herein. As will be seen by the experimental section, formulation with a lubricant, and hydroxypropylcellulose, or a coblend of HPC has now been shown to produce a stable, injection molded component which can be reliably reproduced and injected from the mold with reduced, or no warpage of the shell.

Experiments with Klucel HPC at various percentages, ranging from 30 to 70% have been formulated and tested for the variance in dissolution times. Formulations containing approx. 26% to 63% Klucel's have been found to have similar dissolution times (<2 hours) in both simulated gastric fluid and simulated intestinal fluids.

To ensure a consistent release, the pharmaceutical formulations include various hydrophilic excipients. Preferably, the hydrophilic excipient is one which does not melt at the extrusion temperature, e.g. the lactose, inorganic salts, HPC, HPMC, such as Pharmacoat 603 (an HPMC with a glass transition temperature 175° C.). As noted, these swellable solids are available commercially in a number of grades by molecular weight, for examples 95K, or 80K grades of HPC. A change in the molecular weight of HPC, for instance, should retain the ability to hydrate the shell, but the hydration rate may be slower, i.e. the rate of expansion will be reduced. Hence, a longer dissolution time of the shell and release of the components therein may result. Experiments with Klucel® HPC at various percentages, have been formulated and tested for the variance in dissolution times. Formulations containing 40 to 70% Klucel® have been found to have similar dissolution times.

Inclusion of a lubricant, such as stearyl alcohol enhances flow. It is also found that higher proportions of stearyl alcohol increase the flowability so as to enable molding of thinner walls. The formulation may optionally include surfactants, and disintegrating agents.

EXAMPLES

The invention will now be described by reference to the following examples, which are merely illustrative and are not to be construed as a limitation of the scope of the present invention. All temperatures are given in degrees centigrade; all solvents are highest available purity unless otherwise indicated.

Example 1

Manufacture of multicomponent pharmaceutical dosage forms with pharmaceutically acceptable polymeric compositions as described herein. Example 1 will describe a general process used to mold the various multicomponent capsules and appropriate subunits. Additional pharmaceutical compositions are shown and described below.

| Item number | Material | % w/w |
|---|---|---|
| 1. | Ammonium methacrylate copolymer (Eudragit RL100) | 25.0 |
| 2. | Hydroxypropyl Cellulose (Klucel GF) | 50.0 |
| 3. | Lactose monohydrate | 13.0 |
| 4. | Stearyl alcohol, milled | 12.0 |
|  | Total | 100.0 |

Using a suitable blender mix together:
Item 2. Hydroxypropyl Cellulose (Klucel GF)
Item 3. Lactose monohydrate
Item 4. Stearyl alcohol, milled
to form a homogeneous powder blend.

Set up a suitable co-rotating twin screw hot melt extruder with both a pellet feeder and a powder feeder together with strand cooling equipment and a pelletizer. Fit the selected mold in the injection molding machine. Example processing parameters are as follows:

| Extruder: | |
|---|---|
| Screw speed | 150 rpm (range 100-500 rpm) |
| Temperature of zone 1 (feed zone) | 50° C. (range 30-75° C.) |
| Temperature of zone 2 | 95° C. (range 85-130° C.) |
| Temperature of zone 3 | 100° C. (range 90-135° C.) |
| Temperature of zone 4 | 110° C. (range 95-140° C.) |
| Temperature of zone 5 | 115° C. (range 100-145° C.) |
| Temperature of strand die | 120° C. (range 105-150° C.) |
| Pellet feeder | 0.25 kg/hour (0.2-1.8 kg/hour) |
| Powder feeder | 0.75 kg/hour (0.2-1.8 kg/hour) |
| Strand cooling equipment: | Appropriate for extrusion rate used |
| Pelletiser: | Appropriate for extrusion rate used |
| Injection molder: | Appropriate injection/cooling times, temperature and injection pressure, dependent on machine type and pellet formulation. |

Pre-heat the extruder to the appropriate temperature. Load the pellet feeder with the Ammonium methacrylate copolymer (Eudragit RL100) and the powder feeder with the blend. Start the extruder screws rotating and then start the two feeders. Process the extruded strand along the cooling equipment into the pelletiser and collect the pellets formed.

Input appropriate machine settings and pre-heat the injection molder. Load the hopper with the pellets and mold the multi-components units.

Additional examples or embodiments of this example have been prepared, using the same process steps but with variant formulations as shown below.

The resulting shells from these examples are welded together with a linker unit, as previously described herein, having a composition comprising Eudragit 4135F, 10% hypromellose (HPMC)—Pharmacoat 603, Shin-etsu Chemical Company, and 12% Stearyl alcohol using a maximum weld strength. Unless otherwise indicated a standard weld for RL100 shells is −2.50 mm, 100% amplitude.

With regards to the shell thickness, if no reference to the wall thickness is given, the shell is of 0.5 mm thickness.

The welded capsules, where applicable were tested using either a USP2 or a USP3 dissolution apparatus.

Example 2

| Formulation | % w/w |
| --- | --- |
| Eudragit RL100 | 25.00 |
| Klucel GF | 50.00 |
| Lactose | 13.00 |
| Stearyl alcohol | 12.00 |

Process Conditions

Extrusion/Injection moulding: Extrusion −1 kg/hr die temp. 120° C., 150 rpm screw, torque 46%, die pressure 5 bar; Injection Moulding—partially filled ⅔ 0.5 mm wall section shells, complete mouldings from other pins; 185 C probe temp. Additional Shell Observations: many cracked or incompletely moulded shells, and a polymer knit line was present on all shells. There was also a high degree of breakage on welding.

Dissolution Testing using USP 2, 0.5 mm capsule shells containing an active ingredient, welded at −2.50 mm; a 100% run at 50 rpm in pH 1.2SGF using Disc sinkers demonstrated a release profile which was fairly reproducible and had a detachment ranging from 34-64 minutes for 6 samples tested.

Example 3

| Formulation | % w/w |
| --- | --- |
| Eudragit RL100 | 35.00 |
| Klucel EF | 40.00 |
| Lactose | 13.00 |
| Stearyl alcohol | 12.00 |

Process Conditions

Extrusion/Injection moulding: Extrusion −1.1 kg/hr die temp. 110° C., 200 rpm screw, torque 53%, die pressure 2 bar; Injection Moulding—crack in ¼ of the 0.5 mm wall section shells, complete mouldings from other pins, 175 C probe temp.

Dissolution Testing using USP 2, 0.5 mm capsule shells containing an active ingredient, welded at −2.50 mm; a 100% run at 75 rpm in pH 1.2SGF using Disc sinkers demonstrated a release profile which was very reproducible and had a detachment ranging from 38-50 minutes for 6 samples tested.

Example 4

| Formulation | % w/w |
| --- | --- |
| Eudragit RL100 | 25.00 |
| Klucel EF | 63.00 |
| Stearyl alcohol | 12.00 |

Process Conditions

Extrusion/Injection moulding: Extrusion -1.2 kg/hr die temp. 110° C., 200 rpm screw, torque 35%, die pressure 1 bar; Injection Moulding—satisfactory 0.5 mm wall section shells, Small knit line on some 0.3 mm shells, 180 C probe temp.

Additional Shell observations: Good mouldings, very little cracking.

Dissolution Testing using USP 2, 0.5 mm capsules, welded at −2.50 mm; a 100% run at 50 rpm in pH 1.2SGF using Disc sinkers demonstrated a variable release times from 58 to 100 minutes.

In an alternative embodiment, using the molded 0.5 mm shells from this example, a film coat was added of Eudragit L30D-55. An Aeromatic Aerocoater was used for applying the coating, with standard procedures, at a 6% film coat by weight gain.

The coated shells have not been tested for their release profile in a USP2 or USP3 dissolution apparatus.

Example 5

| Formulation | % w/w |
| --- | --- |
| Eudragit RL100 | 25.00 |
| Klucel EF | 31.50 |
| Klucel JF | 31.50 |
| Stearyl alcohol | 12.00 |

Process Conditions

Extrusion/Injection moulding: Extrusion −1.2 kg/hr die temp. 115° C., 200 rpm screw; torque 41%, die pressure 4 bar; Injection Moulding—satisfactory 0.5 mm wall section shells, 185 C probe temp.

Additional Shell Observations: Very good mouldings, shells are completely clear, no cracking on welding.

Dissolution Testing using USP 2, 0.5 mm capsules, welded at −2.50 mm; a 100% run at 50 rpm in pH 1.2SGF using Disc sinkers demonstrated a very reproducible detachment ranging between 36-40 minutes for 6 samples tested.

Example 6

| Formulation | % w/w |
| --- | --- |
| Eudragit RL100 | 25.00 |
| Klucel EF | 50.00 |

-continued

| Formulation | % w/w |
| --- | --- |
| Lactose | 13.00 |
| Stearyl alcohol | 12.00 |

Process Conditions

Extrusion/Injection moulding: 0.5 mm shells film were made using the conditions noted above, and coated with an Opadry clear sub coat then coated with an Eudragit L30D-55 enteric coat. The coating was done with an Aeromatic Aerocoater and the film coat weight gain was divided into two groups as follows: A=1.5% w/w sub coat; B=2.5% w/w enteric coat; and C=6.0% w/w enteric coat.

Dissolution Testing using USP 3, 0.5 mm capsule shells with a 1.5% sub coat (A) and a 2.5% enteric coat (B) containing an active ingredient, welded at −2.60 mm; a 100% run at lodpm in pH 1.2SGF demonstrated a release profile which was very reproducible and had a detachment ranging from 40-55 minutes for 6 samples tested.

In an alternative embodiment, the 0.5 mm shells of this example were film coated with an Opadry clear sub coat. The coating was done with an Aeromatic Aerocoater, and the capsules were divided into two groups with a film coat weight gain as follows: A=3.8% w/w sub coat; B=7.0% w/w sub coat.

Using USP3 Dissolution testing conditions, the 7% Methocel coated shells of group B, ultrasonically welded at −2.60 mm, 100% amplitude, produced very reproducible release profiles between 45-55 minutes for 6 samples tested.

In another alternative embodiment, the 0.5 mm shells of this example were film coated with Opadry clear sub coat & then over coated with a Eudragit L30D-55 enteric coat. An Aeromatic Aerocoater was used, and the capsules were divided into two groups with a film coat weight gain as follows: A=2.5% w/w sub coat; B=7.5% w/w enteric coat; and C=10.0% w/w enteric coat Using USP3 dissolution testing conditions, a 2.5% subcoat and a 10% L30D55 enteric coat, 6 sample shells ultrasonically welded at −2.50 mm, 100% amplitude at 10 dpm were tested. Their release profile was considered good with a reproducible release (1 outlier) between 80-125 minutes.

In another alternative embodiment the 0.5 mm shells of this example film were coated with an Opadry clear sub coat using an Aeromatic Aerocoater. The resulting film coat weight gain was as follows: A=1.7% w/w sub coat; B=15.3% w/w enteric coat; C=21.3% w/w enteric coat.

Dissolution Testing using USP 3, 0.5 mm capsule shells with a 1.7% sub coat (A) and a 15.3% enteric coat (B) containing an active ingredient, welded at −2.60 mm; a 100% run at 10 dpm in pH 1.2SGF demonstrated a release profile which was very reproducible and had a detachment ranging from 160-190 minutes for 6 samples tested.

In another alternative embodiment, 0.3 mm shells produced using this formulation were film coated with an Opadry clear sub coat then over coated with a Eudragit L30D-55 enteric coat (about 24 hrs between applications). An Aeromatic Aerocoater was used, and the film coat weight gain was as follows A=2.5% w/w sub coat; B=13.3% w/w enteric coat.

Dissolution Testing using USP3, 0.3 mm capsule shells with a 2.5% w/w sub coat (A) and a 13.3% enteric coat (B) containing an active ingredient, welded at −2.50 mm; a 100% run at 10 dpm in pH 1.2SGF (1.5 hrs), pH5.5 SIF (0.5 hrs) then pH6.8 SIF (2hrs) demonstrated release ranging from 85-130 minutes for 6 samples tested.

Example 7

| Formulation | % w/w |
| --- | --- |
| Eudragit RL100 | 25.00 |
| Klucel EF | 61.00 |
| Stearyl alcohol | 12.00 |
| Titanium dioxide | 2.00 |

Process Conditions:

Extrusion/Injection moulding: Extrusion −1.00 kg/hr die temp. 105° C., 200 rpm screw torque 41%, die pressure 1 bar; Injection Moulding—satisfactory 0.5 mm wall section shells; 180 C probe temp.

Dissolution Testing using USP 3, 0.5 mm capsule shells containing an active ingredient, welded at −2.40 mm; at 100% run at 10 dpm in pH 1.2SGF demonstrated a release profile which was variable and had a detachment ranging from 34-95 minutes for 6 samples tested.

Example 8

| Formulation | % w/w |
| --- | --- |
| Eudragit RL100 | 24.00 |
| Klucel EF | 50.00 |
| Stearyl alcohol | 12.00 |
| Succinic acid | 13.00 |

Process Conditions:

Extrusion/Injection moulding: Extrusion 1.00 kg/hr die temp. 110° C., 200 rpm screw torque 46%, die pressure 1 bar, smooth 'glassy' strand. Injection Moulding—0.5 mm; persistent sticking in cavities. A 0.3 mm shell was not attempted.

Example 9

| Formulation | % w/w |
| --- | --- |
| Eudragit RL100 | 24.00 |
| Klucel EF | 50.00 |
| Lactose | 13.00 |
| Stearyl alcohol | 12.00 |
| SDS | 1.00 |

Process Conditions:

Extrusion/Injection moulding: Extrusion −0.73 kg/hr die temp. 110° C., 200 rpm screw torque, 41%, die pressure 2 bar; Injection Moulding—satisfactory 0.5 mm shells at 150 C probe.

Shells of this example have not been tested for their release profile in a USP2 or USP3 dissolution apparatus.

Example 10

| Formulation   | % w/w |
|---------------|-------|
| Eudragit RL100 | 21.60 |
| Eudragit RS100 | 2.40  |
| Klucel EF     | 32.00 |
| Klucel JF     | 32.00 |
| Stearyl alcohol | 12.00 |

Process Conditions:

Extrusion/Injection moulding: Extrusion –1.5 kg/hr; die temperature 120° C., 150 rpm screw; torque 38%; Injection Moulding—satisfactory 0.5 mm shells at 180° C. probe; occasional sticking in mould.

Dissolution Testing using USP 2, 0.5 mm capsule shells containing an active ingredient, welded at –2.50 mm; at 100% run at 75 rpm in pH 1.2SGF using Disc sinkers demonstrated a release profile which was very reproducible and had a detachment ranging from 34-48 minutes for 6 samples tested.

Example 11

| Formulation   | % w/w |
|---------------|-------|
| Eudragit RL100 | 2.40  |
| Eudragit RS100 | 21.60 |
| Klucel EF     | 32.00 |
| Klucel JF     | 32.00 |
| Stearyl alcohol | 12.00 |

Process Conditions:

Extrusion/Injection moulding: Extrusion –1.5 kg/hr; die temperature of about 120° C., 153 rpm screw; torque 35%.; Injection Moulding—satisfactory 0.5 mm shells at 180° C. probe; Occasional sticking in mould.

Dissolution Testing using USP 2, 0.5 mm capsule shells containing an active ingredient, welded at –2.50 mm; a 100% run at 75 rpm in pH 1.2SGF using Disc sinkers demonstrated a release profile which was fairly reproducible and had a detachment ranging from 46-50 minutes for 4 samples and 84 and 94 minutes for 2 samples tested.

Dissolution Testing using USP3, 0.5 mm capsule shells containing an active ingredient, welded at –2.45 mm; a 100% run at 10 dpm in pH 1.2SGF (1.5 hrs) then pH6.8SIF (4.5 hrs) demonstrated a release profile which was very reproducible and had a detachment ranging from 55-80 minutes for 6 samples tested.

Example 12

| Formulation   | % w/w |
|---------------|-------|
| Eudragit RL100 | 10.00 |
| Citric acid   | 20.00 |
| Klucel EF     | 58.00 |
| Stearyl alcohol | 12.00 |

Process Conditions:

Extrusion: Extrusion –1.0 kg/hr; with a die temperature of about 110° C.; a 200 rpm screw; and torque 35%.

All publications, including but not limited to patents and patent applications, cited in this specification are herein incorporated by reference as if each individual publication were specifically and individually indicated to be incorporated by reference herein as though fully set forth.

The above description fully discloses the invention including preferred embodiments thereof. Modifications and improvements of the embodiments specifically disclosed herein are within the scope of the following claims. Without further elaboration, it is believed that one skilled in the area can, using the preceding description, utilize the present invention to its fullest extent. Therefore, the Examples herein are to be construed as merely illustrative and not a limitation of the scope of the present invention in any way. The embodiments of the invention in which an exclusive property or privilege is claimed are defined as follows.

What is claimed is:

1. A dosage form comprising a capsule having a shell with an outer surface and an opposed inner surface, the inner surface defining at least in part a confined space for holding a drug substance, and the outer surface being exposed to a gastro-intestinal environment, the shell being composed of an extruded and injection molded composition comprising
   (i) Ammonio methacrylate Copolymer Type A or ammonium methacrylate Copolymer Type B present in an amount of about 10 to about 80% w/w;
   (ii) at least one dissolution modifying excipient selected from a swellable solid present in an amount of about 20 to about 65% w/w, and wherein the swellable solid is a blend of hydroxypropylcelluloses having differing molecular weights and wherein such blend comprises a low molecular weight hydroxypropylcellulose having a molecular weight of about 80,000 and a high molecular weight hydroxypropyl cellulose selected from a hydroxyproplycellulose having a molecular weight of about 140,000 and a hydroxypropylcellulose having a molecular weight of about 370,000;
   optionally in combination with a second dissolution modifying excipient selected from the group consisting of a
   a) disintegrant present in an amount of about 10 to 40%,
   b) a water soluble filler present in the range of about 5 to about 70% w/w,
   c) a low molecular weight solute present in the range of about 2.5 to about 70% w/w, and
   d) non-reducing sugar present in the range of about 2.5 to about 15% w/w;
   (iii) a lubricant present in an amount of about 5% to about 25% w/w; and
   (iv) optionally a surfactant present in an amount of 0 to about 10%, a plasticizer present in an amount of 0 to about 10% w/w and/or a processing agent present in an amount of 0 to about 10% w/w.

2. The dosage form according to claim 1 wherein the copolymer is Ammonio methacrylate Copolymer Type A.

3. The dosage form according to claim 2 wherein the copolymer is present in an amount of about 15 to about 50% w/w.

4. The dosage form according to claim 2 wherein the copolymer is present in an amount of about 20 to about 40% w/w.

5. The dosage form according to claim 2 wherein the lubricant is stearyl alcohol present from about 10 to about 15% w/w.

6. The dosage form according to claim 1 wherein the surfactant is present in an amount of less than 2% w/w.

7. The dosage form according to claim 6 wherein the surfactant is sodium dodecyl sulphate or is a block copolymer of ethylene oxide and propylene oxide.

8. The dosage form according to claim 1 wherein the lubricant is stearyl alcohol, glycerol monostearate (GMS), talc, magnesium stearate, silicon dioxide, amorphous silicic acid, or fumed silica; and combinations or mixtures thereof.

9. The dosage form according to claim 8 wherein the lubricant is stearyl alcohol.

10. The dosage form according to claim 9 wherein the stearyl alcohol is present from about 10 to about 15% w/w.

11. The dosage form according to claim 1 wherein the lubricant is stearyl alcohol present from about 10 to about 15% w/w.

12. The dosage form according to claim 1 wherein the swellable solid is composed of a blend of hydroxypropyl cellulose polymers, each having a differing molecular weight, present in a total amount of about 30% to about 80% w/w.

13. The dosage form according to claim 1 wherein the second dissolution modifying excipient is a non-reducing sugar, a low molecular weight solute, or a water soluble filler.

14. The dosage form according to claim 13 wherein the second dissolution modifying excipient is selected from the group consisting of xylitol, mannitol, lactose, starch, and sodium chloride, and combinations or mixtures thereof.

15. The dosage form according to claim 1 wherein the second dissolution modifying excipient is a disintegrant.

16. The dosage form according to claim 15 wherein the disintegrant is selected from the group consisting of sodium starch glycollate, croscarmellose sodium, crospovidone (cross-linked polyvinyl pyrrolidone), copovidone, polyvinyl pyrrolidone; and combinations or mixtures thereof.

17. The dosage form according to claim 1 wherein the plasticizer is triethyl cifrate (TEC), tributyl cifrate, acetyl triethyl citrate (ATEC), acetyl tributyl citrate (ATBC), dibutyl phthalate, dibutyl sebacate (DBS), diethyl phthalate, vinyl pyrrolidone glycol triacetate, polyethylene glycol, polyoxyethylene sorbitan monolaurate, propylene glycol, or castor oil; and combinations or mixtures thereof.

18. The dosage form according to claim 1 wherein the processing agent is talc.

19. The dosage form according to claim 18 wherein the processing agent is present in an amount of about 1 to about 5% w/w.

20. The dosage form according to claim 1 which further comprises an absorption enhancer.

21. The dosage form according to claim 20 wherein the absorption enhancer is chitosan, lecithin, lectin, a sucrose fatty acid ester, Vitamin E-TPGS; and combinations or mixtures thereof.

22. The dosage form according to claim 1 wherein the Ammonio methacrylate Copolymer Type A is present in an amount of about 15 to 50% w/w, the lubricant is stearyl alcohol, and the at least one dissolution modifying excipient is a blend of hydroxypropylcelluloses having differing molecular weights.

23. The dosage form according to claim 22 wherein the blend of hydroxypropyl cellulose polymers comprises a hydroxypropylcellulose having a molecular weight of about 80,000 and a hydroxypropylcellulose having a molecular weight of about 370,000.

24. The dosage form according to claim 12 wherein the blend of hydroxypropyl cellulose is a hydroxypropylcellulose having a molecular weight of about 80,000 and a hydroxypropylcellulose having a molecular weight of about 370,000.

25. The dosage form according to claim 22 wherein the blend of hydroxypropyl cellulose is of equal % w/w.

26. The dosage form according to claim 22 wherein the blend of hydroxypropyl cellulose is about 32% w/w.

27. The dosage form according to claim 22 wherein the hydroxypropyl cellulose is present in an amount of about 50% w/w.

28. The dosage form according to claim 22 which comprises a second dissolution modifying excipient which is a wicking agent.

29. The dosage form according to claim 28 wherein the wicking agent is lactose.

30. The dosage form according to claim 29 wherein the lactose is present in an amount of about 13% w/w.

31. A dosage form comprising at least one subcomponent having a wall portion made from an extruded material comprising a pharmaceutical composition selected from the group consisting of:

| # | Formulations | % w/w |
|---|---|---|
| 1. | Eudragit RL100 | 25.00 |
|  | Klucel EF | 31.50 |
|  | Klucel JF | 31.50 |
|  | Stearyl alcohol | 12.00 |
| 2. | Eudragit RL100 | 21.60 |
|  | Eudragit RS100 | 2.40 |
|  | Klucel EF | 32.00 |
|  | Klucel JF | 32.00 |
|  | Stearyl alcohol | 12.00; and |
| 3. | Eudragit RL100 | 2.40 |
|  | Eudragit RS100 | 21.60 |
|  | Klucel EF | 32.00 |
|  | Klucel JF | 32.00 |
|  | Stearyl alcohol | 12.00. |

32. A dosage form according to claim 1, in which the capsule shell has a wall with a thickness in the range of about 0.1-0.8 mm.

* * * * *

UNITED STATES PATENT AND TRADEMARK OFFICE
CERTIFICATE OF CORRECTION

PATENT NO. : 8,147,871 B2
APPLICATION NO. : 11/078077
DATED : April 3, 2012
INVENTOR(S) : Adrian Brown et al.

It is certified that error appears in the above-identified patent and that said Letters Patent is hereby corrected as shown below:

Claim 1, col. 18, line 28, "Ammonio methacrylate" should read -- Ammonium methacrylate --.

Claim 17, col. 19, line 36, both instances of "cifrate" should read -- citrate --.

Claim 22, col. 19, line 54, "Ammonio methacrylate" should read -- Ammonium methacrylate --.

Signed and Sealed this
Seventeenth Day of July, 2012

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 8,147,871 B2 | Page 1 of 1 |
| APPLICATION NO. | : 11/078077 | |
| DATED | : April 3, 2012 | |
| INVENTOR(S) | : Adrian Brown et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1,234 days.

Signed and Sealed this
Eleventh Day of September, 2012

David J. Kappos
*Director of the United States Patent and Trademark Office*

UNITED STATES PATENT AND TRADEMARK OFFICE
CERTIFICATE OF CORRECTION

PATENT NO.       : 8,147,871 B2  
APPLICATION NO.  : 11/078077  
DATED            : April 3, 2012  
INVENTOR(S)      : Adrian Brown et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1,327 days.

Signed and Sealed this
First Day of January, 2013

David J. Kappos
*Director of the United States Patent and Trademark Office*